United States Patent [19]

Gunther et al.

[11] Patent Number: 5,329,942

[45] Date of Patent: Jul. 19, 1994

[54] METHOD FOR FILTERING BLOOD IN A BLOOD VESSEL OF A PATIENT

[75] Inventors: Rolf Gunther, Aachen, Fed. Rep. of Germany; Brian L. Bates, Bloomington, Ind.

[73] Assignee: Cook, Incorporated, Bloomington, Ind.

[21] Appl. No.: 856,114

[22] Filed: Mar. 20, 1992

Related U.S. Application Data

[63] Continuation-in-part of Ser. No. 566,768, Aug. 14, 1990, abandoned.

[51] Int. Cl.⁵ .............................................. A61B 17/00
[52] U.S. Cl. ..................................... 128/898; 606/200
[58] Field of Search ............... 606/200, 198; 128/898

[56] References Cited

U.S. PATENT DOCUMENTS

| | | | |
|---|---|---|---|
| 3,540,431 | 11/1970 | Mobin-Uddin | 128/1 |
| 3,868,956 | 3/1975 | Alfidi et al. | 128/345 |
| 3,952,747 | 4/1976 | Kimmell, Jr. | 128/303 R |
| 3,996,938 | 12/1976 | Clark . | |
| 4,425,908 | 1/1984 | Simon | 128/1 |
| 4,494,531 | 1/1985 | Gianturco | 128/1 R |
| 4,619,246 | 10/1986 | Molgaard-Nielsen et al. | 128/1 R |
| 4,643,184 | 2/1987 | Mobin-Uddin | 128/303 R |
| 4,688,553 | 8/1987 | Metals | 128/1 R |
| 4,832,055 | 5/1989 | Palestrant | 128/899 |
| 4,873,978 | 10/1989 | Ginsburg | 128/345 |
| 4,969,891 | 11/1990 | Gewertz | 606/200 |
| 4,998,539 | 3/1991 | Delsanti | 128/898 |

FOREIGN PATENT DOCUMENTS

| | | |
|---|---|---|
| 2580504 | 10/1098 | France . |
| 2652267 | 3/1991 | France . |
| 2657261 | 7/1991 | France . |

OTHER PUBLICATIONS

Major, Jr. et al., entitled "The Eichelter Catheter," *Arch. Surg.,* vol. 109, Aug. 1974, pp. 278-282.

Driller et al. "New Percutaneous Caval Filter Device for Pulmonary Thromboembolis," *Medical and Biological Engineering,* vol. 14, No. 6, Nov. 1976 pp. 629-635.

*Primary Examiner*—Michael H. Thaler
*Attorney, Agent, or Firm*—Woodard, Emhardt, Naughton, Moriarty & McNett

[57] ABSTRACT

A method of filtering blood in a blood vessel of a patient wherein a catheter is initially introduced into the blood vessel and then advanced to a desired location within the blood vessel. Subsequently, a portion of a positioning assembly having a filter distally attached thereto is guided through the catheter. The filter is then positioned at a location beyond the distal end of the catheter within the blood vessel with the positioning assembly. The positioning assembly is then locked to the catheter. The catheter is then anchored to an object located outside of the blood vessel. Thereafter, an amount of blood is filtered within the blood vessel with the filter. The filter can be readily repositioned by unlocking the positioning assembly from the catheter, repositioning the filter within the blood vessel with the positioning assembly and then relocking the positioning assembly to the catheter.

13 Claims, 6 Drawing Sheets

5,329,942

METHOD FOR FILTERING BLOOD IN A BLOOD VESSEL OF A PATIENT

CROSS-REFERENCE TO RELATED APPLICATION

This application is a continuation-in-part of the commonly owned U.S. patent application Ser. No. 07/566,768 filed Aug. 14, 1990 and entitled METHOD AND APPARATUS FOR FILTERING BLOOD IN A BLOOD VESSEL OF A PATIENT now abandoned.

BACKGROUND OF THE INVENTION

This invention relates generally to a method and apparatus for filtering blood in a blood vessel of a patient.

Blood clot filtering devices have heretofore been provided to filter blood for clots such as emboli and thrombi in a patient's blood vessel. Certain of these devices were designed to be permanently remotely placed in a blood vessel and included an anchoring means to prevent the migration of the filter from one point to another within the blood vessel. Once the filtering device was remotely placed within the vessel, the device was left indefinitely. An example of such a blood clot filtering device is disclosed in U.S. Pat. No. 4,619,246 issued to Molgaard-Nielsen et al. This reference shows the use of a collapsible filter basket adapted to be introduced into a blood vessel for the purpose of entrapping thrombi and emboli in the blood flowing through the vessel. The Molgaard-Nielsen device is designed to be placed remotely within a blood vessel. A plurality of anchoring legs are secured to a filter basket. The free end of each leg is bent outwardly to form a hook. When the filter basket is positioned in a blood vessel, each hook penetrates slightly into the wall of the vessel so as to hold the filter basket in position.

A device described by Driller et al. in a 1976 technical article is another example of a permanently placed vena cava filter. Such device consists of an open cone formed by straight strands of thin stainless steel wire. Each wire strand has three barbs at the tip to hold the filter basket at one location within the vessel. The strands are joined together at a central hub. In order to place the filter, a plug-ended wire guide is inserted into a length of polyethylene tubing. The collapsed filter is placed in the distal end of a length of polyethylene tubing with the filter hub in the proximal position. The plug-end of the wire guide is then brought into contact with hub of the filter. A Touhy clamp is attached to the proximal end of the tubing. The Touhy clamp permits the plug-ended guide to be securely held a few centimeters proximal the filter while the catheter is advanced. In this way the filter will not be inadvertently ejected. The loaded tubing is then introduced into the jugular vein and advanced under fluoroscopy into the subrenal inferior vena cava. The Touhy clamp is loosened and the plug-end of the wire guide is then advanced to contact the filter. The filter is ejected by withdrawing the tube sleeve while the filter is kept stationary during ejection by the plug-ended wire guide. The strands spring out as the tubing is withdrawn from about the filter. The guide wire and tubing are then withdrawn.

Another device which is designed to filter blood for clots in a blood vessel of a patient is described by Major et al. in a 1974 technical article. This device consists of a multiple ribbed catheter which is introduced through the saphenous vein. After passage into the vena cava, the ribs of tile catheter are extended to contact the cava wall. This produces a sieve through which blood will flow but which will entrap emboli. After the filtering portion is positioned in the vena cava, the tubing which extends proximally from the patient's body is severed and the device is left in place indefinitely until the patient's risk of pulmonary embolism had passed.

The above and other similar prior art devices have the disadvantage that the filter remains in contact with the interior wall of the vena cava for a substantial period of time at the same location with the result that the filter becomes endothelialized and hence attached to tile interior wall of vena cava. This condition tends to block flow of blood in the vena cava and often results in trauma to the interior wall of the vein when tile filter is torn free from its attachment with the wall.

SUMMARY OF THE INVENTION

One embodiment of the present invention involves a method for filtering blood in a blood vessel of a patient wherein a catheter is initially introduced into the blood vessel and then advanced to a desired location within the blood vessel. Subsequently, a portion of a positioning means having a filter distally attached thereto is guided through the catheter. The filter is then positioned at a location beyond the distal end of the catheter within the blood vessel with the positioning means. The positioning means is then locked to the catheter. The catheter is then anchored to the patient and blood is filtered. Before the filter has become endothelialized to the blood vessel, the positioning means is unlocked and the filter is repositioned within the blood vessel with the positioning means.

Another embodiment of the present invention involves an apparatus for filtering blood in a blood vessel of a patient which comprises a filter and a positioning means connected to the filter for positioning the filter at a location within the blood vessel. In addition, the apparatus comprises means for guiding a portion of the positioning means within the blood vessel and means for anchoring the guiding means to an object outside of the blood vessel. The apparatus further includes a means for releasably locking the positioning means to the guiding means thereby allowing the filter to be readily repositioned from a certain location to another location within the blood vessel with the positioning means.

One object of the present invention is to provide an improved method and apparatus for filtering blood.

Still another object of the present invention is to provide a method of apparatus for filtering blood in which the filter does not become endothelialized and hence attached to the vena cava wall.

Other objects and benefits of the present invention can be discerned from the following written description and accompanying drawings.

BRIEF DESCRIPTION OF THE DRAWINGS

FIG. 4 shows the apparatus of FIG. 1 partially advanced into a blood vessel of a patient where the filter is expanded and located in the vena cava. FIG. 4 further shows, in phantom, the expanded filter at another location subsequent to repositioning the filter in accordance with the method of the present invention.

FIG. 5A further shows, in phantom, the expanded filter at another location subsequent to repositioning the filter in accordance with the method shown in FIG. 4.

FIG. 5B further shows, in phantom, the the proximal end portion of the positioning assembly of the filtering apparatus at another location subsequent to repositioning the filter in accordance with the method shown in FIG. 4.

DESCRIPTION OF THE PREFERRED EMBODIMENT

Figure 1:
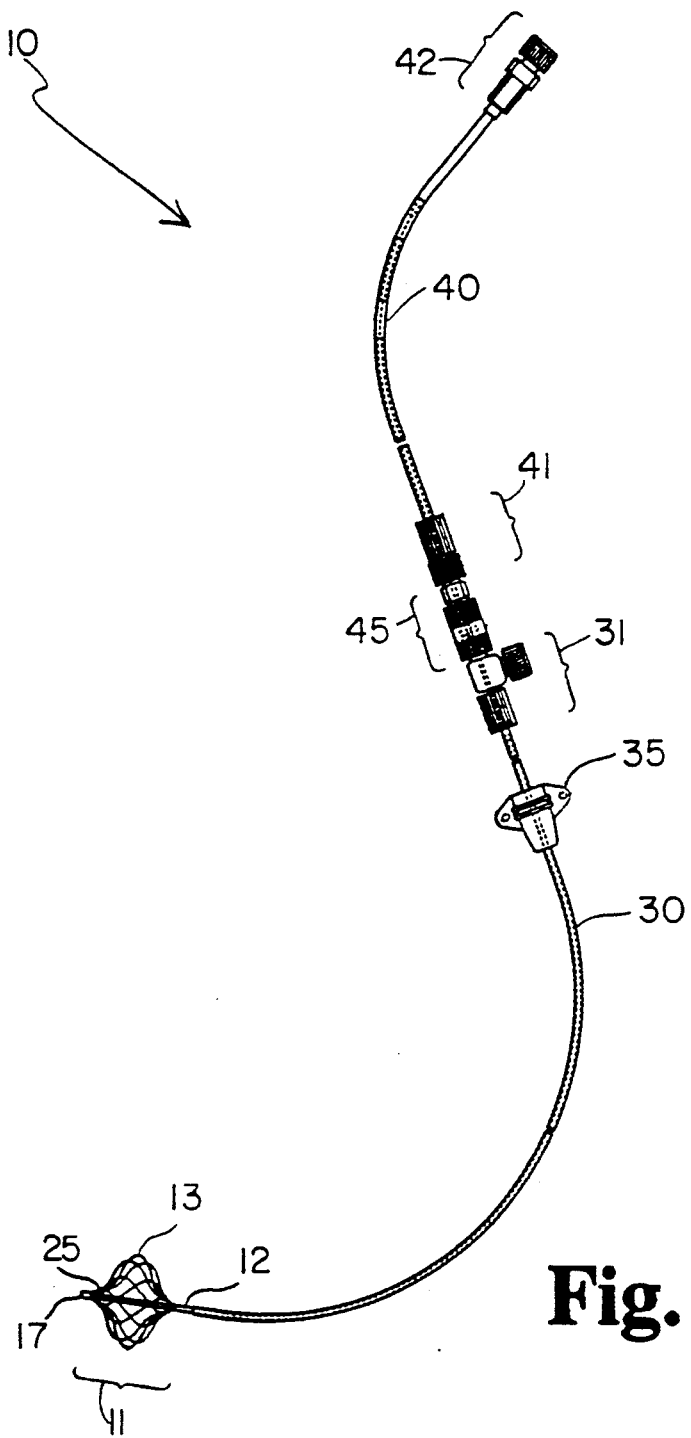
FIG. 1 is a side elevational view of the apparatus for filtering blood in a blood vessel of a patient of the present invention wherein the filter basket is in its expanded and relaxed state and further the sliding lock assembly is in its unlocked position.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices and methods, and such further applications of the principles of the invention as illustrated therein being contemplated as would normally occur to one skilled in the art to which the invention relates.

Referring now to FIG. 1, there is illustrated an apparatus for filtering blood in a blood vessel of a patient which is generally designated by the numeral 10. Apparatus 10 includes a collapsible filter basket 11, a positioning assembly 12, a catheter 30, an anchoring device 35, a connecting tube 40 and a Touhy-Borst fitting 45.

Figure 2:
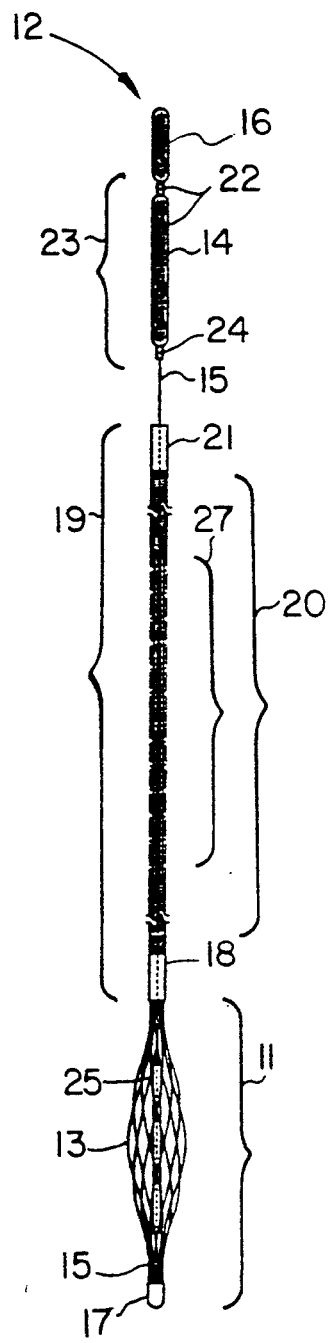
FIG. 2 is a side elevational view of the positioning assembly of the apparatus for filtering blood of FIG. 1 wherein the filter basket is in its collapsed and unrelaxed state and the sliding lock assembly is in its unlocked position.
Figure 3:
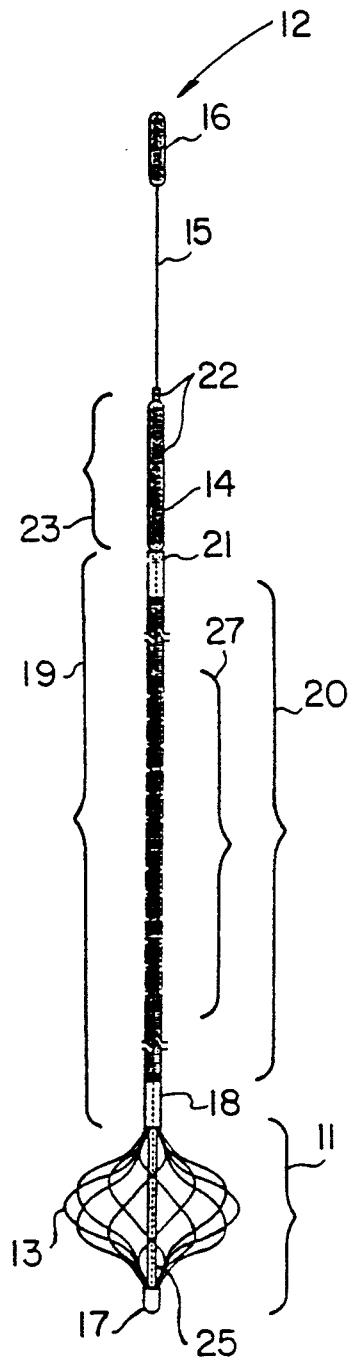
FIG. 3 is a side elevational view of the positioning assembly of the apparatus for filtering blood in a blood vessel of a patient of FIG. 1 wherein the filter basket is in its expanded and relaxed state and the sliding lock assembly is in its locked position.
Figure 4:
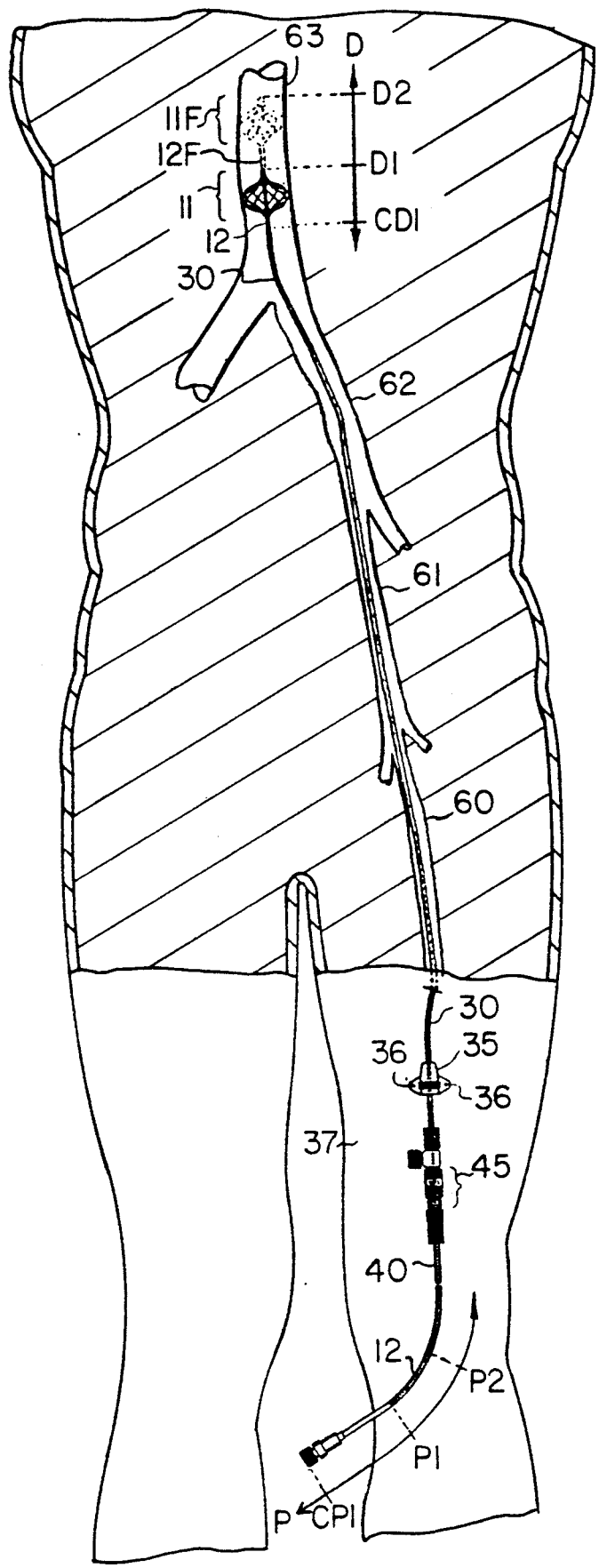
FIG. 4 is a fragmentary, median section through a human body from the left and right thighs upward and illustrates a medical procedure performed in accordance with the preferred embodiment of the present invention.

As shown in FIGS. 2 and 3, filter basket 11 is comprised of a plurality of thin resilient wires 13 composed of a stainless steel alloy. Wires 13 are interconnected at each end of filter basket 11 by means of a pair of ferrules 17 and 18 which are respectively secured to the wires by any appropriate means, such as brazing. Ferrule 17 extends 3.0 millimeters in length while ferrule 18 extends 5.0 millimeters in length. FIGS. 1, 3 and 4 show filter basket 11 in its expanded and relaxed state while FIG. 2 shows filter basket 11 in its collapsed and unrelaxed state. Filter 11 is 3.3 centimeters in length in its expanded state and 6.0 centimeters in its collapsed state. Connected to filter basket 11 is positioning assembly 12 as shown in FIGS. 2 and 3. Positioning assembly 12 comprises a central wire 15, a short segment of wire guide coil 16, a sliding lock assembly 23, a filter expander assembly 19, a short segment of cannula 25 and ferrule 17.

Figure 5A:
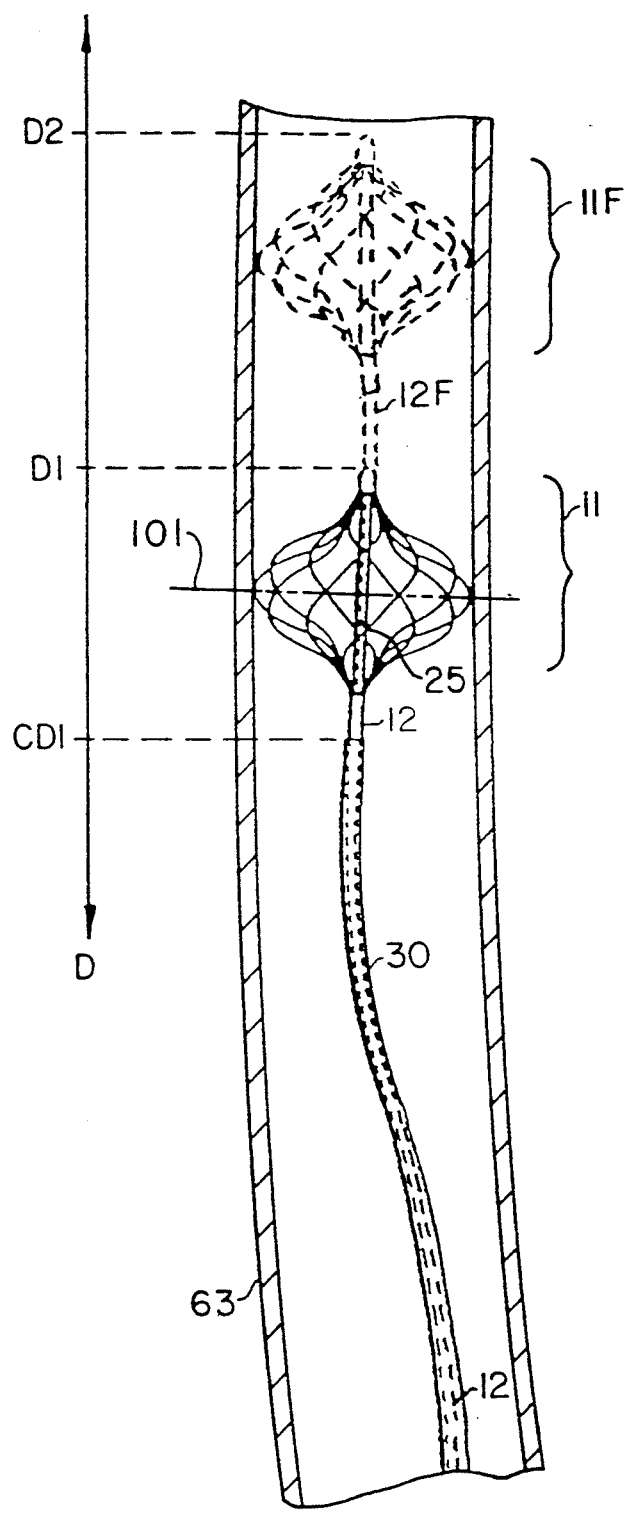
FIG. 5A is an enlarged fragmentary view of the vena cava and distal end portion of the filtering apparatus of FIG. 4.
Figure 6:
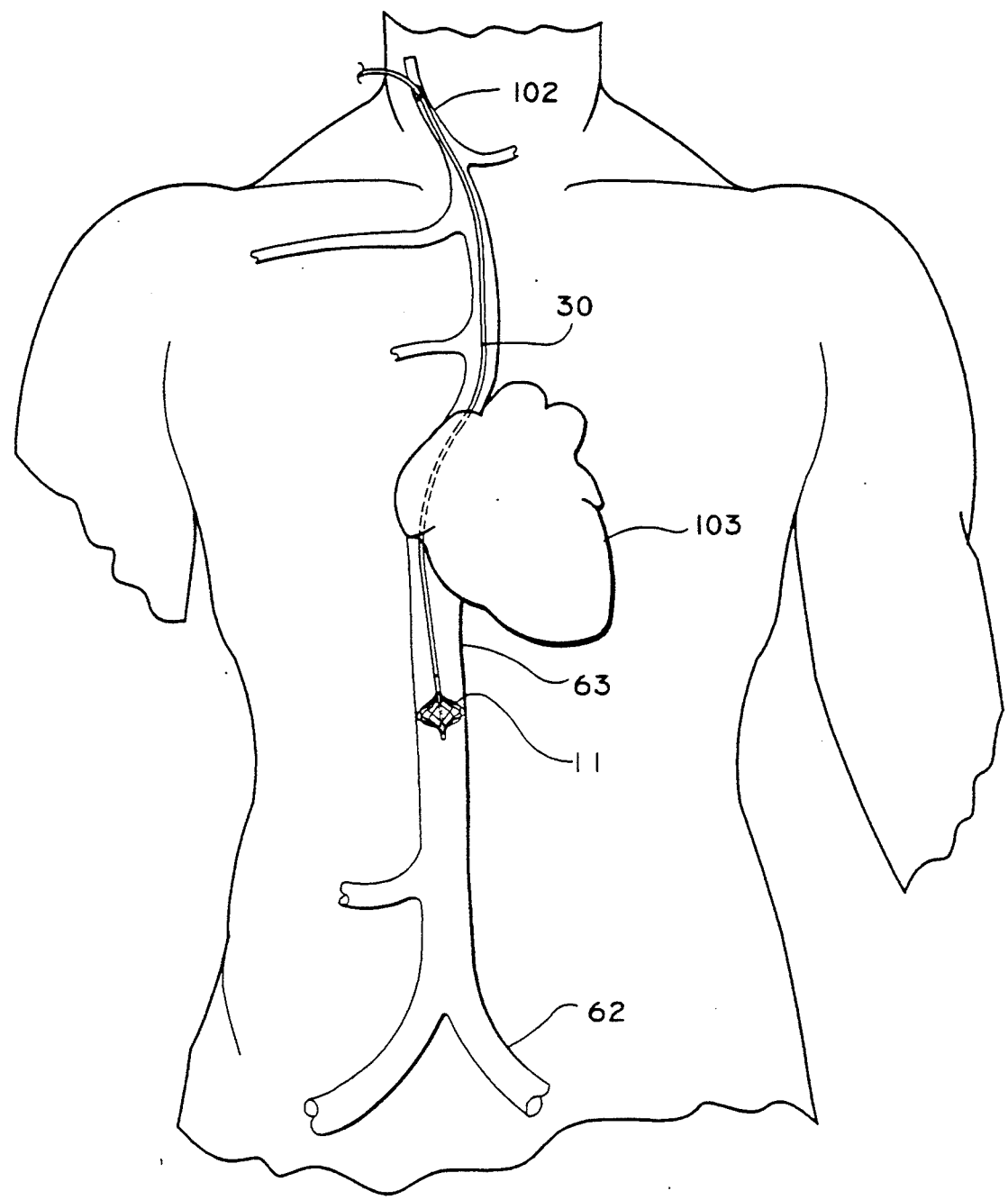
FIG. 6 is a fragmentary section through a human body from left to right and illustrates a medical procedure performed in accordance with another embodiment of the present invention in which the filtering apparatus is positioned in the inferior vena cava by entering the venous system at the juglar vein.

As can be seen in FIG. 5A, filter basket 11 is symmetrical about a hypothetical plane 101 that perpendicularly bisects cannula segment 25, which is disposed within basket 11. Filter basket 11 can be thought of as having two substantially identical halves which are disposed in symmetrical relationship on either side of plane 101. Because of this symmetry, the filtering apparatus of the present invention works equally well when the filter is located either upstream or downstream with respect to the distal end of catheter 30. FIGS. 4 and 6 illustrate this feature of the invention. While the filter basket 11 of both FIGS. 4 and 6 is positioned in the inferior vena cava 63, FIG. 4 shows the blood filter apparatus entering the patient's venous system through the femural vein, and FIG. 6 shows the filter apparatus entering the patient's venous system through the juglar vein 102 and passing through the right atrium of heart 103 to arrive at the inferior vena cava 63. This ability of the present invention is referred to hereinafter as a blood filter apparatus having a reversible filter. Thus, the physician utilizing the present invention has the freedom to choose the best entry point on a particular patient to arrive at the desired filter location from either an upstream or downstream entry point into the body.

Central wire 15 extends 1130 centimeters in length and is connected at one of its ends to ferrule 17 and at its other end to coil segment 16. Coil segment 16 is 1.0 centimeter in length and has an outer diameter of 0.052 inch. Central wire 15 extends through but is not fixedly attached to sliding lock assembly 23, expander assembly 19, filter basket 11 and cannula segment 25.

Expander assembly 19 is comprised of a ferrule 21, a segment of wire guide coil 20 and ferrule 18. Ferrule 21 is 1.0 centimeters in length. Coil segment 20 is 99 centimeters in length and has an outer diameter of 0.052 inch. Coil segment 20 is composed of a stainless steel alloy and has a passageway therethrough as alluded to above. Coil segment 20 is secured at one end to ferrule 18 and at the other end to ferrule 21 by any appropriate means, such as brazing. Ferrules 18 and 21 also have passageways therethrough. Coil segment 20 includes a section 27 in which the coil is stretched as shown in FIGS. 2 and 3. Stretched section 27 extends 20.0 centimeters in length and is located intermediate the ends of coil segment 20. The proximal end of stretched section 27 is 29.0 centimeters in distance from the distal end of ferrule 21.

Cannula segment 25 is positioned concentrically with central wire 15 and within the interior of filter basket 11. The length of cannula segment 25 is 3.0 centimeters. Cannula segment 25 limits the axial displacement of expander assembly 19 toward ferrule 17 along central wire 15. The purpose of this limitation is to allow filter basket 11 to be easily deployed to a desired optimal shape and size without the need for visual aid.

Once filter basket 11 is deployed to its desired optimal shape and size, sliding lock assembly 23 can be used to maintain filter basket 11 in that state. In other words, sliding lock assembly 23 provides a means for maintaining the filter in a desired shape that is independent of both catheter 30 and the inner wall of the blood vessel. Thus, the filter of the present invention can be fully deployed in the blood vessel without the filter applying unwanted pressure to the interior wall of the blood vessel and without any interaction between the filter and the distal end of catheter 30. Sliding lock assembly 23 is comprised of a short segment of wire guide coil 14 and a slightly larger segment of cannula 22. The length of coil segment 14 is 3.5 centimeters and the length of cannula segment 22 is 4.0 centimeters. The outer diameter of coil segment 14 is 0.052 inch. Coil segment 14 and cannula segment 22 each has a passageway therethrough and is concentrically positioned relative to central wire 15. Cannula segment 22 is positioned adjacent and affixed to the interior of coil segment 14. A small portion 24 of cannula segment 22 extends beyond the distal end of coil segment 14. The length of small cannula portion 24 is 0.25 centimeters. Cannula segment 22 has an outer diameter slightly larger than the inner diameter of ferrule 21. The outer diameter of cannula segment 22 is 0.02 inch and tile inner diameter of ferrule 21 is 0.033 inch. As a result, when it is desired to maintain filter basket 11 at its optimal shape and size, sliding lock assembly 23 can be slid over central wire 15 towards ferrule 21 to ultimately wedge small cannula portion 24 of cannula 22 into the interior of the proximal end portion of ferrule 21 thus forcing the interior of small cannula portion 24 to grasp central wire 15 in a friction fit and consequently prevent expander assembly 19 from being proximally axially displaced relative to central wire 15. As a result, since the proximal end of filter basket 11 is secured to the distal end of expander assembly 19, filter basket 11 is thus made highly resistant to collapse. This feature is important because filter baskets encounter various stresses during normal use due to a variety of different loads such as thrombi and emboli. The filter basket 11 is shown locked in its expanded state by sliding lock assembly 23 in FIG. 3.

When it is desired to collapse filter basket 11 such as for insertion into or removal from the blood vessel, sliding lock assembly 23 is pulled axially over central wire 15 toward coil segment 16 thus unlocking expander assembly. 19. Expander assembly 19 is then slid axially over central wire 15 toward coil segment 16 causing the proximal ends of wires 13 to advance axially over central wire 15 toward coil segment 16. The axial movement of the proximal ends of wires 13 toward coil segment 16 correspondingly causes filter basket 11 to collapse and to become longer and thinner. Sliding lock assembly 23 is shown in FIG. 2 in an unlocked position thus allowing filter basket 11 to assume a collapsed state.

Figure 5B:
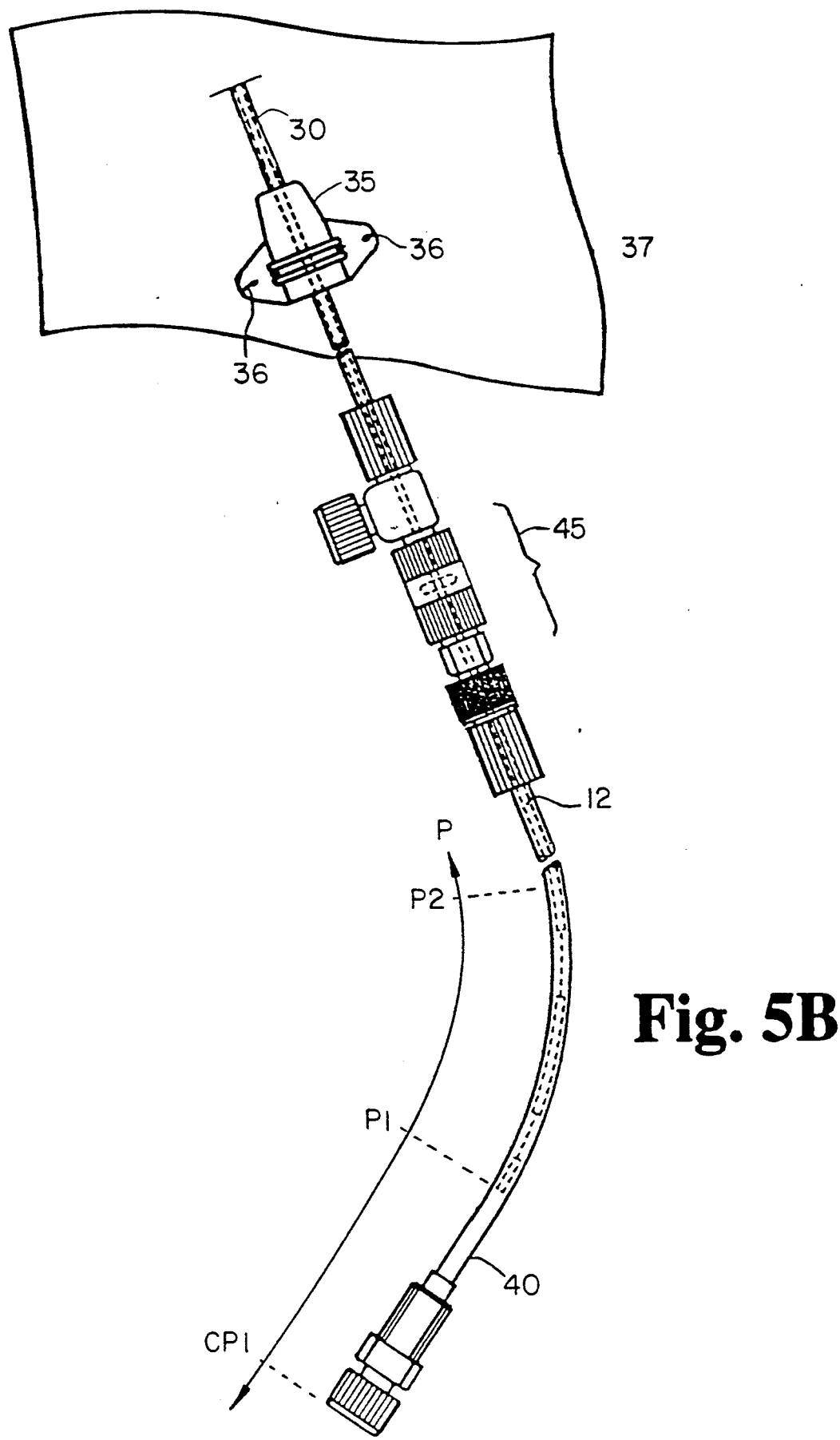
FIG. 5B is an enlarged view of the proximal end portion of the filtering apparatus of FIG. 4.

Catheter 30 is nontapered and open-ended and has a proximal fitting 31 fixed thereon as shown in FIGS. 1 and 4. Catheter 30 is 60.0 centimeters in length and has an outer diameter of 0.092 inch. Fixedly secured to the outer surface and intermediate the ends of catheter 30 is a silicone rubber winged anchoring device 35. The purpose of anchoring device 35 is to anchor apparatus 10 via sutures 36 to the skin 37 of time patient as shown in FIGS. 4 and 5B.

The proximal fitting 31 is releasably attachable to a Touhy-Borst type fitting 45. Such a fitting is a commercially available device, for example, from Cook Inc. of Bloomington, Indiana, Model No. UCC-1 and includes a rubber O-ring that may be squeezed by the operation of the device to grip a wire or other member inside of the rubber O-ring. The fitting 45 is provided to releasably lock positioning assembly 12 to catheter 30 at one of a plurality of positions on the outer surface of stretched section 27 of positioning assembly 12. Stretched section 27 possesses an irregular surface onto which fitting 45 can lock. Since positioning assembly 12 can be locked to catheter 30 at one of a plurality positions, filter 11 can be readily repositioned from a one position to another position within tile blood vessel via positioning assembly 12.

A connecting tube 40 is provided to cover the portion of positioning assembly 12 which extends beyond catheter 30 and fitting 45 in order to maintain the sterility of positioning assembly 12. Connecting tube 40 is 64.0 centimeters in length and has an outer diameter of 0.125 inch. Connecting tube 40 has a proximal fitting 42 and a distal fitting 41 thereon. The distal fitting 41 is provided to releasably attach connecting tube 40 to catheter 30 via Touhy-Borst fitting 45.

A fragmentary, median section through a human body from the left and right thighs upward is shown in FIG. 4 to aid in illustrating a medical procedure performed in accordance with the preferred embodiment of the present invention. In addition, FIGS. 5A and 5B show an enlarged view of the distal and proximal end portions respectively of the blood filtering apparatus 10 as it is used in accordance with the aforementioned medical procedure shown in FIG. 4.

A portion of a nontapered open-ended catheter 30 is introduced into and guided through the femoral vein 60 and advanced through the external iliac vein 61 and the common iliac vein 62 and then into the inferior vena cava 63. The distal end of catheter 30 is advanced to the location CD1 as represented on position indicator D. The catheter can be assisted in initial placement into the femoral vein by a sheath, wire guide and dilator combination. The filter basket 11 and attached positioning assembly 12 (described above and shown in FIGS. 2 and 3) are inserted into the proximal end of catheter 30 with tile filter basket end inserted first. This can be done by collapsing filter basket 11 before insertion with the aid of a short piece of tubing that has the same inner and outer diameters as catheter 30. This short piece of tubing is then removed over the proximal end of positioning assembly 12 and discarded after filter 11 is inside catheter 30.

Filter basket 11 is then advanced through the catheter, and upon exiting the distal end thereof, it changes from a collapsed to an expanded state. Once filter basket 11 is deployed to its expanded state, sliding lock assembly 23 carl be used to maintain filter basket 11 in that state, as described above. The distal end of expanded filter basket 11 is then advanced to the location D1 as represented on position indicator D. When the distal end of filter basket 11 is positioned as above, the proximal end of positioning assembly 12 will correspondingly be at location P1 as represented on position indicator P. In FIGS. 4, 5A and 5B positioning assembly 12 is shown, in phantom, extending through connecting tube 40, fitting 45 and catheter 30. Once filter basket 11 and positioning assembly 12 are positioned at this desired location, the Touhy-Borst fitting 45 is used to lock together catheter 30 and positioning assembly 12. Connecting tube 40 is then slid over the portion of positioning assembly 12 which extends beyond fitting 45 in order to maintain the sterility of the positioning assembly 12. The connecting tube 40 is then secured to fitting 45. Catheter 30 is then anchored to the skin 37 of the patient with sutures 36 via the anchoring device 35. This has the effect of anchoring the entire apparatus 10 at a fixed location.

After the filter has been in place for a period of time, it may be desirable to reposition filter basket 11 within the vena cava to prevent filter basket 11 from becoming endothelialized and hence attached to the interior wall of the vena cava. The design of the present invention allows an operator to readily reposition the filter basket within the vena cava. This is accomplished by removing connector tube 40 from the proximal end portion of positioning assembly 12, loosening fitting 45 to unlock positioning assembly 12 from catheter 30, repositioning positioning assembly 12 and the attached filter basket 11, tightening fitting 45 to relock positioning assembly 12 to catheter 30 and then recovering the proximal end portion of positioning assembly 12 with connecting tube 40.

Referring to FIGS. 4, 5A and 5B, filter basket 11F and a distal end portion 12F of positioning assembly 12 are shown, phantom, at a repositioned location. In this repositioned location, the distal end of filter basket 11F is at location D2 as represented on position indicator D and the proximal end of positioning assembly 12 (not shown) is correspondingly at location P2 as represented on position indicator P. As is shown in FIGS. 4 and 5A tile filter basket contacts the interior wall of the vena cava at different locations after each act of repositioning in accordance with the present invention. Since the filter basket does not become endothelialized to the interior wall of the vena cava with tile above procedure, it can be left in the vena cava for several weeks without damage thereto. It should be noted that before and after the repositioning of the filter basket 11 and attached positioning assembly 12, the location of the distal end of catheter 30 as represented on position indicator D is maintained at CD1. Further, before and after the repositioning of the filter basket 11 and attached positioning assembly 12, the location of the proximal end of connecting tube 40 as represented on position indicator D is maintained at CP1.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method of filtering blood in a blood vessel of a patient comprising the steps of:
   introducing a catheter into the venous system of the patient;
   advancing the catheter through a portion of the venous system to a desired location within the blood vessel;
   guiding through the catheter a portion of a positioning means having a filter distally attached thereto;
   positioning the filter at a desired location beyond the distal end of the catheter within the blood vessel with the positioning means;
   locking the positioning means to the catheter with a locking means;
   anchoring the catheter to an object located outside of the blood vessel;
   filtering an amount of blood within the blood vessel with the filter;
   unlocking the positioning means from the catheter before the filter has become endothelialized to the blood vessel;
   repositioning the filter within the blood vessel at a desired location with the positioning means;
   relocking the positioning means to the catheter; and
   continue filtering blood within the blood vessel with the filter.

2. The method of claim 1 wherein the catheter is introduced into the patient's Jugular vein in the introducing step; and
   is advanced into the inferior vena cava in the advancing step.

3. The method of claim 1 wherein the catheter is advanced into the inferior vena cava in the direction of blood flow in the advancing step.

4. The method of claim 3 wherein the filter is in a collapsed state in the guiding step and in an expanded state in the positioning step.

5. The method of claim 4 wherein the catheter is anchored to the skin of the patient in the anchoring step.

6. The method of claim 5 wherein the catheter is a nontapered open-ended catheter.

7. The method of claim 6 wherein the positioning means is locked to the catheter with a Touhy-Borst fitting in the locking step.

8. The method of claim 7 wherein the catheter is anchored to the skin of the patient with sutures via silicone rubber wings in the anchoring step, 9. The method of claim 1 further including the step of:
   covering the portion of the positioning means which extends proximally beyond the locking means with a connecting tube after the locking step, 10. The method of claim 9 further including the steps of:
    removing the connecting tube that covers the portion of the positioning means which extends proximally beyond the locking means before said unlocking step; and
    recovering the portion of the positioning means which extends proximally beyond the locking means with the connecting tube after said relocking step.

11. A method of filtering blood in a blood vessel of a patient comprising the steps of:
    introducing a catheter into the blood vessel;
    advancing the catheter to a desired location within the blood vessel;
    guiding through the catheter a portion of a positioning means having a filter distally attached thereto;
    positioning the filter at a desired location beyond the distal end of the catheter within the blood vessel with the positioning means;
    deploying the filter to a desired shape;
    securing the filter at the shape to which it was deployed in the deploying step without interaction between the filter and the distal end of the catheter;
    locking the positioning means to the catheter with a locking means, said locking means including means for gripping said positioning means to releasably lock said positioning means to said catheter;
    anchoring the catheter to an object located outside of the blood vessel;
    filtering an amount of blood within the blood vessel with the filter;
    unlocking the positioning means from the catheter;
    repositioning the filter within the blood vessel with the positioning means; and
    relocking the positioning means to the catheter.

12. A method of filtering blood in a blood vessel of a patient comprising the steps of:
  introducing a catheter into the blood vessel;
  advancing the catheter to a desired location within the blood vessel;
  guiding through the catheter a portion of a positioning means having a filter distally attached thereto;
  positioning the filter at a desired location beyond the distal end of the catheter within the blood vessel with the positioning means;
  deploying the filter to a desired shape;
  securing the filter at the shape to which it was deployed in the deploying step without interaction between the filter and the distal end of the catheter;
  locking the positioning means to the catheter with a locking means, said locking means including means for gripping said positioning means to releasably lock said positioning means to said catheter;
  anchoring the catheter to an object located outside of the blood vessel;
  covering the portion of the positioning means which extends proximally beyond the locking means with a connecting tube;
  filtering an amount of blood within the blood vessel with the filter;
  removing the connecting tube that covers the portion of the positioning means which extends proximally beyond the locking means;
  unlocking the positioning means from the catheter;
  repositioning the filter within the blood vessel with the positioning means;
  relocking the positioning means to the catheter; and
  recovering the portion of the positioning means which extends proximally beyond the locking means with the connecting tube.

13. A method of filter blood in a blood vessel comprising:
  providing a filter which is connected to a positioning means;
  positioning the filter in the blood vessel at a desired location;
  fixing the filter in position in the blood vessel by fixing the positioning means relative to the skin of the patient;
  filtering an amount of blood within the blood vessel with the filter;
  releasing the positioning means with respect to the skin of the patient before the filter has become endothelialized to the blood vessel;
  adjusting the position of the filter in the blood vessel by changing the position means relative to the skin of the patient; and
  refixing the filter in the new position in the blood vessel by fixing the positioning means relative to the skin of the patient.

* * * * *

UNITED STATES PATENT AND TRADEMARK OFFICE
CERTIFICATE OF CORRECTION

PATENT NO. : 5,329,942    Page 1 of 2

DATED : July 19, 1994

INVENTOR(S) : Rolf Gunther and Brian L. Bates

It is certified that error appears in the above-identified patent and that said Letters Patent is hereby corrected as shown below:

Column 2, line 16, "tile" should be changed to "the";

Column 4, line 20, "femural" should be changed to "femoral";

Column 4, line 31, "1130" should be changed to "113.0";

Column 5, line 19, "tile" should be changed to "the";

Column 5, line 58, "time" should be changed to "the";

Column 6, line 6, "tile" should be changed to "the";

Column 6, line 37, "tile" should be changed to "the";

Column 6, line 48, "carl" should be changed to "can";

Column 7, line 24, "tile" should be changed to "the";

Column 7, line 28, "tile" should be changed to "the";

Column 8, line 7, "J"ugular should be changed to "j"ugular;

Column 8, line 27, "," should be changed to ".";

Column 8, line 32, "," should be changed to ".";

Column 10, line 8, "filter" should be changed to "filtering";

UNITED STATES PATENT AND TRADEMARK OFFICE
CERTIFICATE OF CORRECTION

PATENT NO. : 5,329,942
DATED : July 19, 1994
INVENTOR(S) : Rolf Gunther and Brian L. Bates It is certified that error appears in the above-indentified patent and that said Letters Patent is hereby corrected as shown below:

Column 10, line 23, "position" should be changed to "positioning".

Signed and Sealed this

Twenty-third Day of May, 1995

Attest:

BRUCE LEHMAN

Attesting Officer

Commissioner of Patents and Trademarks